United States Patent [19]

Harandi et al.

[11] Patent Number: 4,926,003
[45] Date of Patent: May 15, 1990

[54] PROCESS FOR COMBINING THE REGENERATORLESS OPERATION OF TANDEM SUPER-DENSE RISER AND FLUID-BED OLIGOMERIZATION REACTORS CONTAINING A ZEOLITE OLIGOMERIZATION CATALYST

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 422,325

[22] Filed: Oct. 16, 1989

Related U.S. Application Data

[63] Continuation-in-part of Ser. No. 184,465, Apr. 20, 1988, Pat. No. 4,877,921.

[51] Int. Cl.$^5$ .................................................. C07C 2/02
[52] U.S. Cl. .................................... 585/517; 585/533; 585/716; 585/722
[58] Field of Search ................ 585/517, 533, 716, 722

[56] References Cited

U.S. PATENT DOCUMENTS

| | | | |
|---|---|---|---|
| 3,845,150 | 10/1974 | Yam et al. | 208/135 |
| 3,960,978 | 6/1976 | Givens et al. | 585/531 |
| 4,090,949 | 5/1978 | Owen et al. | 208/78 |
| 4,417,086 | 11/1983 | Miller | 585/530 |
| 4,423,268 | 12/1983 | Miller | 585/533 |
| 4,456,779 | 6/1984 | Owen et al. | 585/415 |
| 4,542,247 | 9/1985 | Chang et al. | 585/254 |
| 4,605,807 | 8/1986 | Mazurek | 585/517 |

FOREIGN PATENT DOCUMENTS

85/05102  11/1985  European Pat. Off. .

*Primary Examiner*—Curtis R. Davis
*Attorney, Agent, or Firm*—Alexander J. McKillop; Charles J. Speciale; L. G. Wise

[57] ABSTRACT

A high pressure process is disclosed for oligomerizing a lower olefin-containing feed to produce distillate or lubes without having to regenerate spent catalyst. Directly coupling the operation in tandem of a MOG (Mobil Olefin to Gasoline) riser reactor and a fluid bed MODL (Mobil Olefin to Distillate or Lubes) reactor, each containing a medium pore size siliceous metallosilicate crystalline shape selective zeolite catalyst, and each operating so that the effluent from each leaves in the super-dense phase, produces the desired product. The MOG riser operates in the transport regime at sufficiently high severity so as to make a "distillate-rich" gasoline effluent with spent catalyst from the MODL reactor. The MODL reactor operates in the turbulent regime at low severity, with catalyst having a lower coke content than that of riser catalyst, to produce a major portion by wt of either distillate or lubes, depending upon the chosen mode of operation, with excellent per pass conversion of olefins. Substantially no catalyst from the riser goes to the fluid bed, while a minor portion of the inventory of catalyst in the fluid bed is either intermittently or continuously withdrawn as a slipstream. This slipstream may be drawn down into the riser, or discharged to a FCC unit, or both. A gasoline/distillate splitter separates gasoline from distillate and/or lubes made in the MODL reactor. A portion of the gasoline is purged, but the remainder is recycled to the inlet of the MODL reactor to quench the effluent from the MOG riser before it is introduced into the MODL reactor. This control of temperature, and avoiding the use of a regenerator provides an economic process.

24 Claims, 3 Drawing Sheets

PROCESS FOR COMBINING THE REGENERATORLESS OPERATION OF TANDEM SUPER-DENSE RISER AND FLUID-BED OLIGOMERIZATION REACTORS CONTAINING A ZEOLITE OLIGOMERIZATION CATALYST

BACKGROUND OF THE INVENTION

This application is a continuation-in-part of application Ser. No. 250,660 filed Sept. 29, 1988 which teaches a two-stage process for upgrading olefinic light gas feedstock (termed "light gas" for brevity herein) containing $C_2$–$C_5$ lower, particularly $C_3$–$C_5$, olefins (alkenes) and paraffins (alkanes); and also, Ser. No. 184,465 filed Apr. 20, 1988 which teaches the oligomerization of $C_2$+ olefins in a single reaction zone of catalyst, present as a turbulent fluid bed in which olefins in the super-dense phase are oligomerized (hence "super-dense" reactor).

This invention relates to a two-stage process utilizing a known oligomerization catalyst in each of two super-dense reactors in tandem, each of which operates to generate an effluent at sufficiently high temperature and pressure to be in the super-dense condition defined herebelow.

Because super-dense effluent from a MOG (for "Mobil Olefin to Gasoline") riser reactor (or, simply "riser") flows directly into the MODL (for "Mobil Olefin to Distillate and/or Lubes") reactor (referred to as such when reference is made to its operation either in a distillate mode to make a major fraction of distillate, or in a lubes mode to make a major fraction of lubes), the super-dense reactors truly operate in tandem; and, operation in tandem dispenses with a regenerator for spent catalyst (hence "regeneratorless", or the neologism "regenless" for ease, convenience and brevity). When the MODL secondary, fluid-bed reactor operates in a distillate mode, it is referred to herein as a "MOD" reactor; and, when this MODL reactor operates in a lubes mode, it is referred to as a "MOL" reactor. The MODL reactor may, under specific, generally atypical circumstances, also be operated to produce both gasoline and distillate in an effluent ("MODL effluent") which contains a larger proportion by weight (wt) of gasoline than is present when the reactor is operated in the distillate mode. Under such operating conditions the secondary reactor is referred to as a "MOGD" (for "Mobil Olefin to Gasoline & Distillate") reactor.

Operation of the regenless process with tandem super-dense reactors provides hitherto unattainable flexibility and stability of operation, particularly with respect to (i) the wide range of feedstocks which may be used, (ii) the efficiency with which a first, riser reactor may be operated at high severity in the transport mode, (iii) the economy inherent in the elimination of intercoolers and other equipment, including a regenerator, for "spent" catalyst, (iv) the ability to guard the catalyst in the MODL reactor against undue contamination which is countered in the MOG riser, and (v) the high conversion to distillate and/or lubes obtained at low severity in a fluid bed reactor operating under super-dense conditions in the turbulent sub-transport regime.

The extent to which the operation of a regenerator influences the complexity and cost of operating an olefin oligomerization process at a relatively much higher pressure than that of the regenerator, may be appreciated by studying the disclosure of our copending patent application Ser. No. 286,204 filed Dec. 19, 1988. In the particular instance where an oligomerization reactor is operated under super-dense conditions, both physical equilibria and practical considerations dictate that a spent catalyst stream be stripped, for example with steam, and regenerated at a relatively much lower pressure than that at which the super-dense fluid bed reactor operates. Such a process requires the use of lock-hoppers between the reactor and the regenerator, to lower the pressure, and, also between the regenerator and the reactor, to charge the regenerated catalyst from a low pressure zone to a much higher pressure zone.

Despite improvements in regeneration and the process scheme using lock-hoppers, regeneration is still a demanding and expensive unit operation, and much effort has been directed towards configuring a process which dispenses with the use of a regenerator, as for example, disclosed in our copending patent application Ser. No. 339,466, filed Apr. 17, 1989.

An ancillary consideration is the amount of carbonaceous residue ("coke") deposited on the catalyst as an undesirable byproduct of the oligomerization reaction The less deposited, the smaller the cost of regeneration. But the amount of coke deposited is a function of numerous operating conditions, and no prior art reference teaches how operation of a reactor in "plug" flow (characteristic of a riser reactor) might affect coke formation, as compared to coking up of the same catalyst in a turbulent fluid bed. Clearly, if no coke is formed, no regeneration would be required. But as long as there is substantial coke formation, operation of a continuous oligomerization process demands that some steps be taken to cope with the coke formation.

The first stage of the regenless process comprises upgrading either light gas, FCC gas, and/or, light naphtha, boiling range 175° C. (347° F.) to 240° C. (464° F.), any one of which contains at least 10 percent by weight (% by wt) olefins, to intermediate range hydrocarbons boiling in the range from 50° C. to 204° C. (125° F.–400° F.) ("gasoline") in a primary riser reaction zone.

The key to economic operation of our process is the excellent conversion, in excess of 90%, which we obtain despite operating a riser in the transport regime, because the fluidizing medium at least in the upper portion of the MOG riser reactor and throughout the fluid bed MODL, is neither gas nor liquid, but a supercritical fluid in the super-dense phase. The phase of the feed to the MOG riser is not critical and may be gas, or liquid under high pressure, the latter being immediately vaporized upon initiation of the exothermic oligomerization reaction. However, it is essential that the upper portion of the reactor be in the super-dense phase, and that the effluent leaves in the super-dense phase. Therefore the MOG riser will be referred to herein as being in the super-dense phase.

In contrast with a typical transport riser reactor operating in the gaseous phase, in which the suspended solids are in the range from 1 to about 5% by volume, we can operate a super-dense riser with solids in the range from 10 to 30%, and because of the physical properties of the super-dense fluidizing medium, we can maintain a satisfactory dispersion in each zone of the riser at much lower superficial velocities than in a prior art gas-phase transport regime.

We thus obtain the advantages of dilute-phase fluidization under transport conditions with much higher "solids density", that is, less voidage, than in a prior art transport zone. By "dilute-phase fluidization" I refer to a condition in which there is a net flow of fluid through the disperse suspension, but no net flow of solids; the particles move about in the suspension but do not flow along with the gas stream, or the reactor would empty. When the fluid velocity is further increased, the particles flow along with the gas at a particle velocity approximately equal to the differential increase in gas velocity. Under such transport conditions the reactor does empty; to maintian a solids inventory, particles must be continually fed to the reactor with the inlet fluid.

Though our '660 application disclosed that the MOG primary reactor used therein may be operated as a riser reactor, a fluid bed was used. Since the operating pressure was relatively low, operation of a riser at such pressure would not be expected to pose a problem. The concept of operating a riser, or any portion of a riser, under super-dense conditions simply did not occur to us because it was hard to conceive of plug flow under super-dense conditions. In plug flow, there is essentially no back-mixing in the axial direction, and very little, if any, mixing in the radial directions. The homogeneous distribution of catalyst, the isothermal conditions, and the narrow range of distribution of the hydrocarbon components in a turbulent fluid bed, are so different from the conditions in a riser reactor, that the added limitation of super-dense conditions made operation of the MOG riser unpredictable; and, tying its operation to a fluid bed MODL reactor, also operating under super-dense conditions, more so.

In particular, under plug flow conditions, there was no basis upon which we could predict how the catalyst would perform at the high WHSV required for a riser operating with a super-dense phase, necessarily with plug flow, and at pressure and temperature conditions at which it is critical that there be no liquid phase present. Nor did we fully appreciate the engineering requirements of controlling a riser operating in the super-dense phase, or, with the lower portion operating in the mixed phase and the upper portion operating in the super-dense phase.

The super-dense phase is defined by operating conditions such that no liquid may be present, or, above those at which liquid may be present, hence referred to herein as $P_{max}$ and $T_{max}$. Such operating conditions prevail at near-critical and super-critical pressure and/or temperature in the super-dense phase which is always present in the upper portion of the riser, so that the effluent leaves under super-dense conditions. By "near-critical" we refer to a pressure which is typically at least 2857 kPa (400 psig), and a temperature which is typically at least 204° C. (400° F.); such conditions are always present for the effluent, but not necessarily always above the critical temperature of the feed. It will be appreciated that the pressure of the feed to the riser will always be above the operating pressure of the MODL if they are to operate in tandem. In other words, the reactor converts light gas to heavies in a single zone operating at a pressure and temperature outside a tightly circumscribed region of pressure and temperature ("critical P & T region") which region lies near, or above the apex of a phase diagram defining the critical point ($P_{cr}$, $T_{cr}$) of the mixture of hydrocarbons in the reactor.

Each super-dense reactor in this process operates best when the effluent from each is in the supercritical pressure and temperature region, at a pressure which is about 3550 kPa (500 psig) or above, and a temperature which is about 204° C. (400° F.) or above. The hope that the selectivity and yield of a riser under such conditions might be favorable, was tempered by the realization that a riser operating under high severity conditions would be deemed impractical from an economic point of view.

The super-dense MOG fluid-bed reactor in our '660 case, was operated at relatively low weight hourly space velocity ("WHSV", it being understood that WHSV signifies pounds of olefins fed per pound of zeolite per hour) but otherwise under process conditions generally within the ranges specified for those used in a process described in our U.S. Pat. No. 4,777,316, except that we operated the '660 MOG reactor to produce higher conversion to gasoline, and a "distillate-rich" gasoline (at least 1 part distillate for 10 parts by wt gasoline) effluent substantially free of aromatics (that is, less than about 3 mol percent aromatics), which effluent contained slightly more paraffins than in our '316 process. Further, the effluent in our '660 application was condensed and fractionated under conditions different from those in our '316 process so that we avoided sending ($C_{10}+$ and heavier) components to the secondary reactor thus providing a tailored, olefin-rich $C_5+$ feed, substantially free of distillate, to a secondary reactor in which the feed is converted either to distillate, or to lubes depending upon the particular preselected mode in which the secondary reactor is operated.

Though we also suggested using a super-dense MODL reactor we failed to recognize that, (i) directly flowing the "distillate-rich" effluent from the MOG reactor to the MODL reactor without changing the phase of the effluent, did not adversely affect selectivity and yield in the MODL reactor; and (ii) after high activity catalyst from the MODL reactor was "used" (or "spent"), the useful life of the "spent" catalyst as an oligomerization catalyst, could be beneficially, effectively prolonged, if this catalyst was directly transferred to the riser reactor.

Despite the overlap in the operating conditions of pressure and temperature for both the MOG and the MODL reactors in the disclosures of some of our preceding inventions, we did not recognize the "doability" of operating a super-dense MOG riser with plug flow (transport regime), let alone the benefit of doing so. Nor did we realize that we could do so without sacrificing the catalyst's selectivity and conversion of $C_2$–$C_5=$ when the riser was operated to produce a "distillate-rich" MOG effluent. Nor did we know the particular operating conditions for operating a fluid-bed MODL reactor with a tailored $C_5$–$C_9$ feed which produces more distillate than gasoline.

"Distillate" refers to $C_{10}+$ hydrocarbons boiling in the range from 130° C. to 343° C. (266° F.–650° F.); "lubes" refers to hydrocarbons boiling above 343° C. (650° F.) having a viscosity in the range from 4 cp to about 40 cp, measured at 100° C. The particular operational mode chosen depends upon which particular boiling range of oligomerized product is desired, though in either the MOD or MOL modes, a minor amount of $C_5+$ gasoline range hydrocarbons may also be formed. When this occurs, the gasoline, typically not a desired product in our process, is recycled to the MODL reactor to yield the desired distillate or lubes product. Light gas containing a substantial, preferably a major portion, typically more than 75% of combined propene and butenes, is a particularly well-suited feed to the reactor.

The specific embodiments of this invention derive from operating the MOG riser reactor as a recirculating ("recirc" for brevity) riser with partially "coked" catalyst which is obtained from the MODL fluid-bed reactor. Conditions in each reactor are such that only the olefins are oligomerized. Operation of the reactors in tandem provides the flexibility to operate the process to produce mainly distillate, or lubes, or even gasoline in the secondary reactor, but always producing a "distillate-rich effluent" from the MOG riser reactor. Tailoring the super-dense upper portion of the MOG riser to provide an effluent for the fluid bed MODL reactor results in a surprisingly effective combination of conventional unit operations which permit continuous operation of the process. In this "maximum conversion" operation of the MOG reactor, an exceptionally high conversion of light gas (or, FCC gas), or light naphtha to olefins is obtained at WHSV > 10 hr$^{-1}$.

Feeding distillate-rich effluent formed in the MOG riser to the fluid bed MODL does not diminish the yield of distillate produced in the MODL despite some expected cracking of distillate in the MODL; and, after separating the distillate, the remaining gasoline-containing stream is recycled to the MODL reactor. But for this combination of a gasoline-containing recycle and distillate-rich MOG riser effluent to the MODL reactor, we would not have the unexpectedly economic oligomerization of olefins in the MODL reactor, along with beneficial processing flexibility and savings in the costs of operation, all of which help make the process economical.

Except for means to separate entrained catalyst in the distillate-rich effluent to the MODL reactor, we now dispense with equipment to process the MOG effluent to the MODL reactor. As explained in the '660 case, the thrust was to remove distillate from the distillate-rich effluent before flowing the gasoline to the MODL reactor. A process scheme to do so required providing a debutanizer, and placing a gasoline/distillate splitter ("G/D splitter") or a high temperature separator ("HTS") before the MOD reactor in the distillate mode. We dispense with the equipment.

Developments in fluid-bed and fixed bed catalytic processes using a wide variety of zeolite catalysts have spurred interest in commercializing the conversion of olefinic feedstocks to $C_5^+$ hydrocarbons including gasoline, diesel fuel, lubes, etc. In addition to the discovery that the intrinsic oligomerization reactions are promoted by aluminum metallosilicate (hereafter, "ZSM-5 type") zeolite catalysts, several discoveries relating to implementing the reactions in an apt reactor environment, have contributed to the success of current processes. These are environmentally acceptable processes for utilizing feedstocks containing lower olefins, especially $C_3$–$C_5$= (olefins), though a significant quantity, up to 40% ethylene, along with olefins and paraffins heavier than $C_5$ may also be present. A predominantly olefinic light gas containing more than 50% by wt, and preferably more than 60%, of combined propene and butenes, is a particularly well-suited feed to oligomerization reactors using a ZSM-5 type catalyst. It will be recognized that the higher the content of $C_2H_4$ and $C_3H_6$ in the feed to the MOG riser, the higher its operating pressure.

In our MOG+MODL combination of tandem super-dense riser+fluid-bed reactors, it is essential that the former operates with a relatively lower activity catalyst than the latter, at WHSV > 10 hr$^{-1}$, under relatively high (top) temperature conditions in its upper half; and that the latter operates with a relatively higher activity catalyst than the former, at WHSV < 10 hr$^{-1}$, under relatively low temperature conditions.

In addition to the operational flexibility referred to hereinabove, afforded by the combination of tandem super-dense riser+fluid-bed reactors, our process results in a sufficiently low "coke-make" to permit regenless operation. A slipstream of spent catalyst is either intermittently or continuously withdrawn from the riser reactor and flowed to a fluid catalytic cracking (FCC) cracker.

Dispensing with spent catalyst from the MOG riser in this fashion is practical because of the favorably low coke make, and the high conversion which results from operation above $P_{max}$ and at or above $T_{max}$; also, because the entire contents of the MOG riser is in the transport regime, and the fluid-bed is in a turbulent regime, the solid acts both as catalyst and heat transfer medium to maintain isothermal conditions. In this process, the superdense fluid is neither gas nor liquid, but for convenience and familiarity, we treat the oligomerization reaction as being a gas/gas reaction.

More particularly, the MOG riser reactor operates continuously to oligomerize light gas containing propene, butenes and pentenes, preferably in the absence of added hydrogen, to a $C_{10}^+$ rich hydrocarbon stream, with higher pressure in the riser than the MODL fluid-bed, whichever its mode of operation.

In the MOD mode, the reactors are operated at relatively low pressure in the range from about 2857 kPa to about 10436 kPa (400 psig-1500 psig), and relatively high temperature in the range from 260° C. to about 371° C. (500° F.-700° F.). In the MOL mode the reactors are operated at relatively high pressure in the range from about 5270 kPa to about 13881 kPa (500 psig-2000 psig), and relatively low temperature in the range from 204° C. to about 315° C. (400° F.-600° F.). Even higher pressures, as high as 20821 kPa (3000 psig) may be used if the economics of operating at such high pressure can be justified by the lube "make".

The combination of MOG and MODL reactors in tandem is uniquely effective because the MOG reactor functions as a "guard" reactor for the MODL. Because of the sensitivity of a ZSM-5 type of catalyst to basic nitrogen-containing organic compounds such as alkylamines (e.g. diethylamine), or, to oxygenated compounds such as ketones, it is important to protect the catalyst in the MODL reacator. It will be recognized that alkylamines are used in treating light gas streams, and ketones are typically present in Fischer Tropsche-derived light ends streams, both of which streams are particularly well-suited for upgrading by oligomerization. This sensitivity (poisoning), is a characteristic of the catalyst under the process conditions of prior art olefin oligomerization processes, particularly the fixed bed processes operated at high pressure. Such processes require the addition of hydrogen as a preventitive antidote. Though our process is not adversely affected by the presence of hydrogen, there is no readily discernible economic incentive for using hydrogen in either the primary-stage or secondary-stage reactors, and we prefer not to do so.

Though the earliest prior art, moderate-pressure processes, for example those disclosed in U.S. Pat. Nos. 3,827,968 and 3,960,978 to Givens et al, used a zeolite catalyst to oligomerize lower olefins under moderate conditions, and produced excellent conversions to distillate range olefins in a fixed bed microreactor, some over-riding problems relating to operating the process economically were not foreseen (see "Conversion of $C_2$–$C_{10}$ Olefins to Higher Olefins Over Synthetic Zeolite ZSM-5" by W. E. Garwood presented at the Symposium on Advances in Zeolite Chemistry before the Division of Petroleum Chemistry, Inc., American Chemical Society, Las Vegas Meeting Mar. 28–Apr. 2, 1962).

The '978 patent discloses that low alpha ZSM-5 and ZSM-11 catalysts not only have reduced activity for cracking n-hexane and other paraffins, but also produce less than 10% by wt aromatics. The runs were made in a fixed bed microreactor, and, at that time, it was not known that the process required the addition of hydrogen to control coke deposition and to prevent poisoning of the catalyst by nitrogen-containing organic impurities. The basic knowledge that low activity ZSM-5 and ZSM-11 type catalysts effectively oligomerized lower olefins, was used to arrive at improvements in "Catalytic Conversion of Olefins to Higher Hydrocarbons" in U.S. Pat. No. 4,456,779 to Owen et al. which discloses oligomerization of olefins in a MOD reactor system of three downflow fixed beds, in series, with intercoolers; and, more recently, in "Conversion of LPG Hydrocarbons to Distillate Fuels or Lubes Using Integration of LPG Dehydrogenation and MOGDL" in U.S. Pat. No. 4,542,247 to Chang et al which discloses fixed beds in a two-stage catalytic process for converting paraffins to olefins which in turn are converted to gasoline and distillate. The first stage MOG reactor is operated under conditions given in U.S. Pat. Nos. 3,960,978 and 4,211,640 to Givens et al. Under these conditions there is a substantial make of aromatics which are undesirable if the effluent from the MOG is to be converted to distillate (aromatics lower the cetane number, among other things).

In the '779 process, multiple fixed bed reactors are used, each operating in the same range of process conditions, and it was essential to dilute the feed to the reactors with both lower alkanes and recycled gasoline, to maintain a controllable exotherm in the bed. To provide the gasoline recycle, the effluent from the operating reactors (a spare reactor is always being regenerated) is debutanized after oligomerization of olefins is completed. Moreover, the fixed-bed processes in both the '247 and '779 patents require the addition of hydrogen for the reasons given hereinabove. Thus, despite operation at as high a pressure as is economically feasible, the use of hydrogen with a high concentration of lower alkanes dictates that the oligomerization be carried out in the gaseous phase, or vapor/liquid phases, thus aggravating both the heat transfer and mass transfer problems. When we use a fluid-bed MODL reactor, it operates with the hydrocarbons in the super-dense phase, the precise conditions of operation, being determined by economics.

Because Chang et al first dehydrogenated a paraffinic feed, they typically converted 30–40% of the paraffins to olefins. The feed to the MOG reactor therefore was predominantly $C_3$/$C_4$ paraffinic, as was the effluent from the MOG reactor, since the undehydrogenated $C_3$/$C_4$ paraffins are not oligomerized. Because, after oligomerization in the '247 fixed bed MOG reactor, the effluent still contained a major proportion of $C_3$/$C_4$ paraffins, Chang et al had to separate the paraffins from the olefins in the effluent (so that the separated $C_4^-$ paraffins could be recycled to be dehydrogenated).

Since, under their conditions, the make of $C_{10}^+$ components was relatively small, they failed to realize the criticality of separating the $C_{10}^+$ components before the effluent from the MOG reactor was further oligomerized.

Though neither Owen et al, nor Chang et al, knew it at the time, in practice, a fixed bed requires the addition of a substantial quantity of hydrogen (for the reasons given), which fixed bed nevertheless is far less effective than a fluid bed for the specific purpose of "cleaning up" the MOG effluent. It is this volume of hydrogen which adds to the already large volume of diluents being used as a heat sink, albeit an inefficient one. Nothing in either the '779 or the '247 patents suggests the surprising benefits of operating with a fluid bed in the absence of added hydrogen and fluidized with a feed containing too little alkanes to serve as a significant heat sink, namely less than about 50% by wt, preferably less than 30% by wt.

The earlier references disclosed that the product distribution from an MOGD reactor may be tailored by controlling process conditions, such as temperature, pressure and space velocity. Gasoline ($C_5$–$C_{10}$) is readily formed at elevated temperature (preferably about 400° C.) and pressure from ambient to about 2900 kPa (420 psia), preferably about 250 to 1450 kPa (36 to 210 psia). Olefinic gasoline could be produced in good yield and may be recovered as a product; or, it could be fed to a low severity, high pressure reactor system for further conversion to heavier distillate-range products. Distillate mode operation could be employed to maximize production of $C_9^+$ aliphatics by reacting the lower and intermediate olefins at high pressure and moderate temperature. Operating details for typical MOGD oligomerization units are disclosed in U.S. Pat. Nos. 4,456,779 and 4,497,968 (Owen et al); 4,433,185 (Tabak); 4,456,781 to Marsh et al; and U.S. Pat. No. 4,746,316 to Avidan et al.

None of the foregoing alternatives disclosed the technical and economic difficulties of operating a riser MOG reactor under super-dense conditions, or of the fluid-bed MODL reactor also under super-dense conditions, in tandem with the riser MOG reactor.

The combination of tandem super-dense MOG riser+MODL fluid-bed reactors is unexpectedly effective because the riser rids the feed of poisons just as effectively as if it was a fluid-bed, while operating under high severity conditions which nevertheless produce the maximum conversion of olefins to $C_5^+$ olefins, substantially free of aromatics, economically. Since, in addition to the MOG riser effluent, only a gasoline-containing stream (after separation of the distillate) is to be recycled to the fluid bed MODL reactor, poisoning of the MODL catalyst is essentially negated. Because a substantial portion of the coke formation takes place in the MOG fluid bed, our MODL reactor operates with so little coke deposition that spent MODL catalyst can be reused in the MOG riser. Regeneration of the spent catalyst from the riser reactor can be avoided by reusing the spent MOG catalyst in the FCC reactor.

U.S. Pat. Nos. 4,417,086 and 4,417,087 to Miller teach a two-zone reactor operating in the transport mode where the relative superficial gas velocity is greater than the terminal velocity in free fall. Though the operation of a fluid-bed is illustrated (example 2 in each of the '086 and '087 patents) note that no operating pressure is stated in the former, and that operating pressure in the latter is 10 psig (24.7 psia, 170 kPa). The general disclosure that the processes may be operated at a pressure in the range from subatmospheric to several hundred atmospheres, but preferably 10 bar or less, and most preferably 0 to 6 bar, (see middle of col 6 in '086, and, near top of col 5 in '087) is not so ingenuous as to be meant to apply equally to the fixed bed (example 1 of '086 and '087, each illustrates 34.5 bar, 500 psi) and the 170 kPa fluid-bed.

In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al have also contributed to the understanding of catalytic olefin upgrading techniques and have contributed improved processes as in U.S. Pat. Nos. 4,150,062, 4,211,640 and 4,227,992. The '062 patent discloses conversion of olefins to gasoline or distillate in the range from 190°–315° C. and 42–70 atm; and this, and the '640 and '992 disclosures are incorporated by reference thereto as if fully set forth herein.

SUMMARY OF THE INVENTION

We have discovered a process for directly coupling the operation in tandem of super-dense MOG primary (riser) and MODL secondary (fluid-bed) oligomerization reactors, each containing a medium pore size siliceous metallosilicate crystalline acid shape selective zeolite catalyst, the MOG reactor operating in the transport regime at sufficiently high severity so as to make a "distillate-rich" gasoline effluent; and the MODL reactor operating in the turbulent regime at low severity, to make a major portion by wt of either distillate or lubes, depending upon the chosen mode of operation. Under certain circumstances, the fluid-bed may be operated to produce a predominantly gasoline effluent. In each primary or secondary stage, there is very little production of paraffins and essentially no aromatics, while a major amount of the olefins fed to each reactor is converted.

It is therefore a general object of this invention to provide a process in which operating a MOG riser reactor and a MODL fluid-bed in tandem, so that the effluent from each is in the super-dense phase, produces a surprisingly high per pass conversion of olefinic feedstock to either distillate or lubes, such that the weight of distillate or lubes is greater than that of gasoline. Substantially no catalyst from the riser goes to the fluid bed, while a minor portion of the inventory of catalyst in the fluid bed is either intermittently or continuously withdrawn as a slip-stream. This slipstream may be drawn down into the riser, or discharged to a FCC unit, or both.

It is also a general object of this invention, to operate tandem super-dense riser and fluid-bed oligomerization reactors, to oligomerize either an olefinic light $C_5$-$C_7$ naphtha or an olefinic $C_2$+ light gas, for example a LPG feed stock containing from 10–40% by wt $C_2$-$C_5$=, but preferably one containing a major molar proportion of $C_3$-$C_4$= with a minor amount (less than 50%) by wt of $C_2$+ paraffins, and less than 30 mol % hydrogen, to yield either distillate or lubes, without adding hydrogen in the process.

It is a specific object of this invention to provide a riser "recirc" reactor and a fluid-bed reactor operating in tandem, each operating above $P_{max}$ and $T_{max}$; the riser operating at high severity at WHSV in the range from about 10 to about 80 hr$^{-1}$, with "high coke" catalyst having an average coke content in the range from about 3% to about 15% by wt coke, based on the wt of catalyst, and relatively low activity, so that a major amount by weight of $C_5$+ ($C_5$ and heavier hydrocarbons) is produced in the MOG riser effluent. The pentane to pentene weight ratio in the riser effluent is less than 0.4, preferably less than 0.2 ($C_5$:$C_5$= <0.2:1), and a minor amount of $C_4$⁻ hydrocarbons. The MODL fluid-bed operates at a lower pressure than the MOG, at a WHSV in the range from about 0.1 to about 10 hr$^{-1}$, preferably 0.5 to about 5 hr$^{-1}$, with a "low coke" catalyst having an average coke content in the range from about 0.1% to about 10% by wt coke, preferably less than 3% by wt, and relatively high activity, so that an effluent containing distillate and/or lubes is produced. The catalyst in each reactor has a fines content of from about 5% to about 20% by wt, being preferably less than about 10%, based on the wt of the catalyst in the reactor, the fines having a particle size less than 32 microns.

In the distillate mode, the process includes (i) separating the MOD effluent (so referred to because of operation of the reactor in the distillate mode) using a fractionator (gasoline-distillate "G/D" splitter) and/or other separating means, to provide a $C_5$+ olefin-rich gasoline overhead which is at least partially recycled to the MOD reactor, and (ii) recovering a distillate product as bottoms.

In the lubes mode, the process includes (i) separating the MOL effluent (so referred to because of operation of the reactor in the lubes mode) with a G/D splitter and/or other separating means, to provide a $C_5$+ olefin-rich gasoline overhead which is at least partially recycled to the MOL reactor; (ii) recovering a distillate product as a sidestream, a fraction of which may be recycled with the gasoline; and, (iii) recovering a lubes product as bottoms. The fluid-bed MOL reactor produces a high, commercially significant, yield of lubes. In either the distillate or lubes mode, the MODL reactor operates without sacrificing its ability to provide better than 60% selectivity to either distillate or lubes.

Whichever the mode of operation, the MOG riser recirc reactor contains the same ZSM-5 or "zeolite beta" type of catalyst, as does the MODL reactor, but the former operates under high severity conditions, at from about 3550 kPa (500 psig) to 14000 kPa (2000 psig) and above about 10 hr$^{-1}$ WHSV, with a superficial vapor velocity of from 1.5 to 18 m/sec (5–50 ft/sec), with a top outlet temperature above about 316° C. (600° F.), preferably in the range up to about 399° C. (750° F.), to convert at least 60% by wt, preferably at least 80% by wt, of the $C_3$-$C_4$ olefins in the feed-stock to $C_5$+ olefins at high severity conditions with a low activity (equilibrated alpha in the range from 1 to 10) catalyst, but which conditions also produce less than 10% by wt of $C_2$⁻ hydrocarbons.

In the distillate mode, the fluid-bed MOD reactor operates with a low coke catalyst, under low severity conditions, at lower pressure than the riser reactor, but in the same range, with allowance for pressure drop through equipment, and below about 10 hr$^{-1}$ WHSV, a superficial vapor velocity of from to 0.03–0.6 m/sec (0.1–2 ft/sec), and an average bed temperature above about 204° C. (400° F.) preferably in the range up to about 315° C. (600° F.), to convert at least 60% by wt, preferably at least 80% by wt, of the $C_3$-$C_4$ olefins in the feedstock to $C_5$+ olefins but which conditions also produce less than 10% by wt of $C_2$⁻ hydrocarbons.

In the lubes mode, the fluid-bed MOL reactor operates under conditions analogous to those recited for the distillate mode, except that the MOL reactor is operated to produce more lubes than distillate. Whether in the distillate or the lubes mode, at least a portion of the gasoline made in the process is recycled unless the fluid-bed reactor is operated deliberately to enhance the gasoline make, rather than distillate or lubes.

It is a more specific object of this invention to operate tandem MOG riser and MODL fluid-bed reactors in the super-dense phase with an olefin partial pressure greater than about 790 kPa (100 psig), and with (i) catalyst in the MOG riser having a higher coke content than that of catalyst in the MODL fluid bed, (ii) different temperatures, (iii) one-way only catalyst transfer from MODL fluid bed to MOG riser reactor, and (iv) a pressure drop of less than 950 kPa (50 psig) therebetween; so as to produce an MOG riser effluent comprising less than 40% by wt $C_4^-$ olefins, the remaining olefins being $C_5^{+=}$, none of which is separated, but together flowed to the MODL fluid bed.

It is another specific object of this invention to operate a super-dense fluid bed MODL reactor with a gasoline recycle feedstream substantially free not only of aromatics and $C_5^-$ components, but also of $C_{10}^+$ components, so as to maximize conversion of gasoline to distillate. The use of a liquid gasoline recycle to quench the effluent from the MOG reactor provides a means to control the MODL temperature, as well as to avoid the use of a heat exchanger train otherwise used to preheat the recycle stream.

Yet other specific objects of this invention are to combine the operation of tandem MOG and MODL reactors to maximize the production of distillate from a lower olefin-containing light gas, or light naphtha, by not removing $C_{10}^+$ distillate made in the MOG riser reactor; by withdrawing enough spent catalyst from the MODL reactor to maintain the level of coke lower than 10% by wt; to introduce the spent MODL catalyst into the MOG riser reactor where selectivity and conversion is not sacrificed by the higher level of coke on the catalyst; to separate catalyst from oligomerized effluent without stripping the catalyst in either reactor; and, to remove, either intermittently or continuously, and dispose of substantially the same amount of spent MOG riser catalyst, as the amount of fresh catalyst added to the MODL reactor, thus avoiding the costs of regenerating the spent catalyst.

BRIEF DESCRIPTION OF THE DRAWING

The foregoing and other objects and advantages of our invention will appear more fully from the following description, made in connection with the accompanying drawings of a preferred embodiment of the invention, wherein:

FIG. 3 is a flow diagram for the process in the distillate mode, schematically illustrating the tandem relationship of a MOG riser recirc reactor with an MOD fluid-bed reactor; and, a G/D splitter placed downstream of the MOD reactor to recycle gasoline to the MOD reactor Spent catalyst from the fluid bed MOD reactor is either discharged to an off-site FCC unit (not shown), or, flowed to the MOG riser. A slipstream of spent catalyst from the riser is removed from the system and flowed to the FCC unit, or otherwise disposed of.

DETAILED DESCRIPTION OF PREFERRED EMOBDIMENTS

Figure 1:
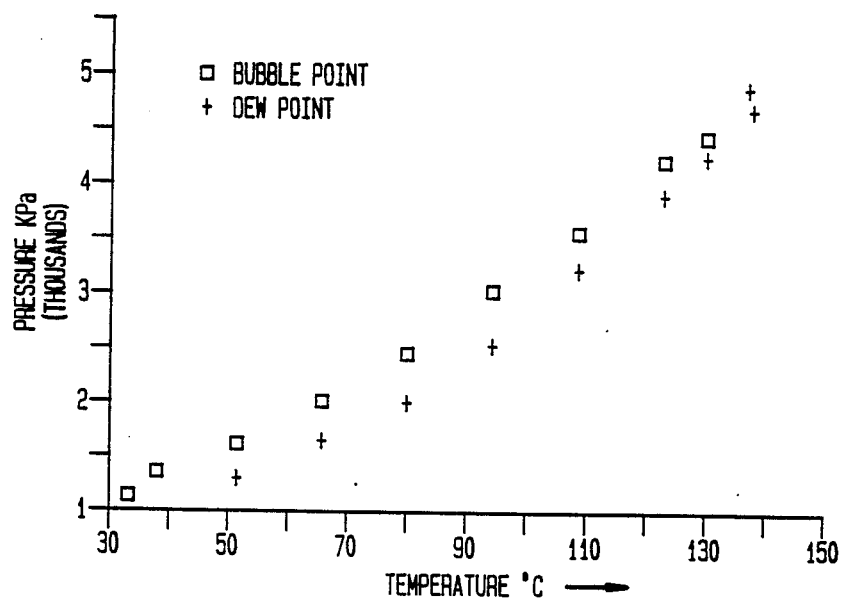
FIG. 1 is a phase diagram showing a plot of dew-point and bubble-point curves for a typical light gas feedstock to be up-bubble-point curves for a typical light gas feedstock to be up-graded.

In a preferred embodiment, the process comprises oligomerizing an olefin-containing feedstream consisting essentially of "light gas" containing $C_2^+$ (ethene and heavier), but preferably, predominantly $C_3^+$ olefins, to a "heavies" product ($C_{10}$ hydrocarbons), by operating tandem super-dense MOG riser+MODL fluid-bed reactors above $P_{max}$ and $T_{max}$, by flowing the light gas feedstream through the riser reactor.

The catalyst in the transport bed in the MOG riser, and the fluid-bed in the MODL, consists essentially of a finely divided ZSM-5 type catalyst having a constraint index in the range from 1 to 12. The activity of the fresh catalyst introduced to the MODL is not narrowly critical provided olefins in the feed to the MODL is oligomerized. Fresh catalyst having an activity (alpha) in the range from about 50 to 600 may be used, as may be previously steamed catalyst with an activity in the range from 10 to 50 provided it is essentially coke-free. When the average coke content of the MODL fluid bed is in the range from 0.1% to about 10%, based on the wt of catalyst, a slipstream is withdrawn either continuously or intermittently, and flowed to the MOG riser. Steam deactivation of catalyst in either the MOG or the MODL reactors is of little concern because there is no regeneration of the catalyst.

The spent (because it is partially deactivated) catalyst withdrawn does not have a uniform coke content because it includes some fresh catalyst, some permanently deactivated catalyst, and the remainder at various stages between. A catalyst sample is therefore said to have an equilibrated or "average" coke content. The equilibrated coke content of catalyst in the MOG riser is in the range from about 3% to about 15%, and that of catalyst in the MODL fluid-bed is in the range less than 10% by wt, preferably less than 3% by wt, diminishing to essentially 0% for fresh catalyst at initial start up.

Though in general, the more the higher the coke content of catalyst, the lower its activity "alpha", the activity is not necessarily correlatable to the amount of coke deposited on the catalyst, because the history of the catalyst must be taken into consideration, particularly if it has been subjected to steam. Thus a catalyst with less than 1% by wt coke may have alpha<10; yet a catalyst with as much as 5% by wt coke may have alpha>10. A catalyst with as much as 15% by wt coke may provide a useful low activity MOG catalyst with alpha in the range from 1 to about 10.

The super-dense phase of the hydrocarbons leaving the MOG riser and entering the MODL fluid bed may be visualized thus. When a vapor at a given pressure is cooled, liquid just commences to form at the temperature for which that pressure is the saturation value; this principle is utilized in the dew-point method for determining vapor pressures of a typical light gas to be converted into a 'heavies' product for which the dew-point is similarly determined. Dew-point is defined as the temperature at which condensation of the vapor in the atmosphere takes place.

Referring now to FIG. 1 there is shown a plot of dew-point and bubble point curves in a phase diagram for temperatures ranging from about 37.8° C. (100° F.) and about 689 kPa (100 psia), to the critical point, about 132° C. (270° F.) and 4272 kPa (620 psia), of a typical light gas feed having the following composition:

| | |
|---|---|
| $C_3^=$ | 25.5% by wt. |
| $C_3$ | 7.6% |
| $C_4^=$ | 43.7% |
| $C_4$ | 23.14% |

It is evident from the phase diagram for the feed, that above about 965 kPa (140 psia) there is less than about 23° C. (50° F.) separating the gas and liquid phases. The difference in temperature becomes progressively smaller as the pressure increases, becoming zero at the critical point.

The critical P & T region is defined by an arc circumscribed around the critical point, between the vertical through the critical point, and, the dew point curve of the phase diagram, the arc having a radius corresponding to about 344.5 kPa (50 psia). It is critical that the dew-point curve never be traversed. In other words, P & T conditions for operation of the process must ensure or the intermediates formed during the reaction. Such conditions obtain at super-critical pressure and near-critical or supercritical temperature conditions.

The "make" of the process is sensitive to operating pressure above $P_{max}$ and at or above $T_{max}$ within the broad range of from about 2857 kPa to about 13880 kPa (400–2000 psig), and particularly in the high pressure mode from 5200 to 13880 kPa (750–2000 psig). Preferred operation excludes a region circumscribed by about a 50 psia differential from $P_{cr}$, $T_{cr}$ of the hydrocarbon mixture in the bed, and bounded by the portion of the bubble-point/dew-point curve downwardly inclined from said point. Under such high pressure conditions, the reaction is prejudiced in favor of oligomerization with a minimum of cracking of alkanes, so that particular ranges of temperatures are found most desirable for a "make" in a specific hydrocarbon boiling range (gasoline, distillate or lubes). The precise optimum combination of pressure and temperatures, along with WHSV, for a particular catalyst, is best arrived at with such trial and error as one skilled in the art is enured to.

Figure 2:
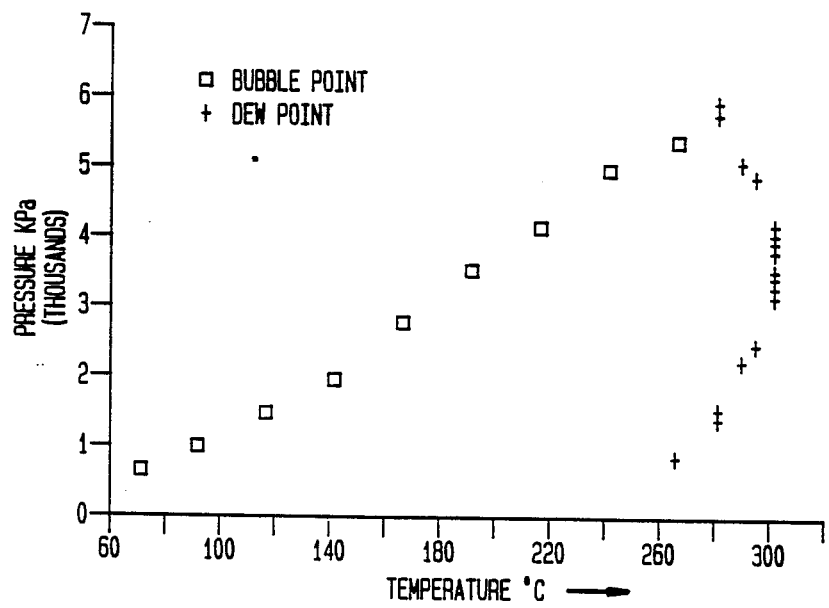
FIG. 2 is a phase diagram showing a plot of dew-point and bubble-point curves for a desirable MOD reactor effluent produced from a desirable gasoline effluent produced in the MOG riser reactor.

With the particular feed characterized by the phase diagram given in FIG. 1, the reactors may be operated in a distillate mode to produce a distillate characterized by the phase diagram shown in FIG. 2. For such operation, "supercritical" refers to a pressure which is at least 3550 kPa (500 psia), so long as the temperature is above $T_{max}$, the temperature at, or above which no liquid may be present. As will be seen by reference to FIG. 2, the more the lower portion of the bubble point curves inwards from the vertical, the lower the pressure at which one can operate at or above $T_{max}$. In operation with light gas, the operating pressure is preferably above 3550 kPa (500 psig), and temperature is about 265° C. (510° F.).

Since operating conditions of each reactor are chosen so that no liquid is formed during the reaction, it is essential that not only the more expanded phase envelope (compared to the relatively narrow one for the feed) for the product be considered, but also all phase envelopes for the hydrocarbon intermediates formed during the reaction. The product contains heavier molecules made during the reaction, so that the phase envelope for the product is distinguishable over that for the feed in that the former is now relatively expanded, and shifted towards higher temperatures. When the desired product selectivity is obtained at a temperature above that corresponding to the dewpoint curve of the product, and above at least 204° C. (400° F.), the optimum (low) pressure may be used to minimize equipment cost. The operating pressure for the lubes mode, is preferably substantially above $P_{cr}$ for the lubes product. The combination of operating process conditions chosen will depend upon the particular specifications of product desired. Oligomerization of the feed is effected in a single zone in each reactor.

Referring further to FIG. 2, the phase diagram shown is for the distillate identified herebelow, over a range of temperature and pressure ranging from about 65.5° C. (150° F.) and about 1240 kPa (180 psia), to the critical point, which is at about 282° C. (540° F.) and 5994 kPa (870 psia).

| | |
|---|---|
| $C_2^=$ | 0.03% by wt. |
| $C_3^=$ | 0.09% |
| $C_3$ | 7.6% |
| $C_4^=$ | 1.19% |
| $C_4$ | 23.14% |
| $C_5$–$C_9$ | 28.96% |
| $C_{10}^+$ | 38.99% |

It is evident from the phase diagram in FIG. 2 that the phase envelope has been expanded, relative to that for the feed (FIG. 1), and shifted towards higher temperatures. There is a much wider spread of temperature between the dew-point and bubble point curves at any given pressure except within about 689 kPa (100 psia) from $P_{cr}$. The difference in temperature becomes progressively smaller as the pressure increases, becoming zero at the critical point. The dewpoint curve for the product is more vertiginous than that for the feed, actually showing a convex favored.

The operating conditions for the MOG riser reactor to produce a distillate-rich gasoline effluent is as follows:

| | |
|---|---|
| Temperature (top) | 316° C.–391° C. (600° F.–750° F.) |
| WHSV | 10–80 hr$^{-1}$ |
| Pressure (inlet) | 5600–6890 kPa (865–1000 psia) |

The operating conditions for the MOD fluid-bed reactor to produce the foregoing distillate product is as follows:

| | |
|---|---|
| Temperature (top) | 260° C.–343° C. (500° F.–650° F.) |
| WHSV | 0.1–10 hr$^{-1}$ |
| Pressure (inlet) | 5600–6750 kPa (815–980 psia) |

The operating conditions for the MOL fluid-bed reactor to produce the foregoing lubes product is as follows:

| Temperature (top) | 205° C.–316° C. (400° F.–600° F.) |
| WHSV | 0.1–10 hr$^{-1}$ |
| Pressure (inlet) | 6300–6890 kPa (915–1000 psia) |

There is no hydrogen introduced to either the MOG or the MODL reactors. It will be understood that the inlet temperature is typically lower than the temperature of the effluent from the MOG reactor because the reaction exotherm raises the temperature, and heat transfer to the MODL fluid bed is controlled to maintain the desired bed temperature by the gasoline recycle, because in the preferred mode, no cooling coils are used in the reactor.

Operation of a riser reactor with a transport zone of medium pore aluminosilicate catalyst, and a ZSM-5 type in particular, at supercritical pressure and at or above $T_{max}$ is unique.

The bed density of our super-dense phase transport bed is in the range exceeding 32 kg/m$^3$ (2 lb/ft$^3$), up to about 640 kg/m$^3$ (40 lb/ft$^3$), preferably less than 320 kg/m$^3$ (20 lb/ft$^3$). The bed density of our super-dense phase turbulent fluid-bed is in the range exceeding 160 kg/m$^3$ (10 lb/ft$^3$), up to about 1120 kg/m$^3$ (70 lb/ft$^3$). The preferred particle density is preferably in the range from about 1.2–2.5 g/cc. A typical super-dense transport bed has a minimum transport velocity of 1 m/sec (3 ft/sec) and operates at a superficial velocity in the range from about 1.5–17 m/sec (5–50 ft/sec), preferably 3.36–7 m/sec (10–20 ft/sec). Conversion of olefins in the riser reactor is at preferably least 80%, and typically in the range from 90–95% or higher.

It is found, that upon operation of the tandem reactors for an extended period of time, the concentration of fines in the riser will be less than that in the fluid bed because fines are carried out of the riser, but in the early portion of the period, the fines content of the riser may be as high as 15%.

A typical super-dense fluid bed has a minimum fluidization velocity of 0.014 m/sec (0.047 ft/sec) and operates at a superficial velocity in the range from about 0.03–0.61 m/sec (0.1–2 ft/sec). The bed densities and superficial velocities for operation of each bed in the lubes mode will typically be different for that just given for the distillate mode, though both will be in the ranges stated hereinabove.

By virtue of the turbulence experienced in the turbulent regime, contact of catalyst particles with the super-dense phase in the MODL reactor is improved, providing at least 80% conversion of $C_4$–$C_{10}$ alkenes, enhanced selectivity, and temperature uniformity. Contact of the super-dense reactants with catalyst particles in the turbulent regime is so good that it results in more than 80%, and more typically, 90% of the olefins being converted.

Figure 3:
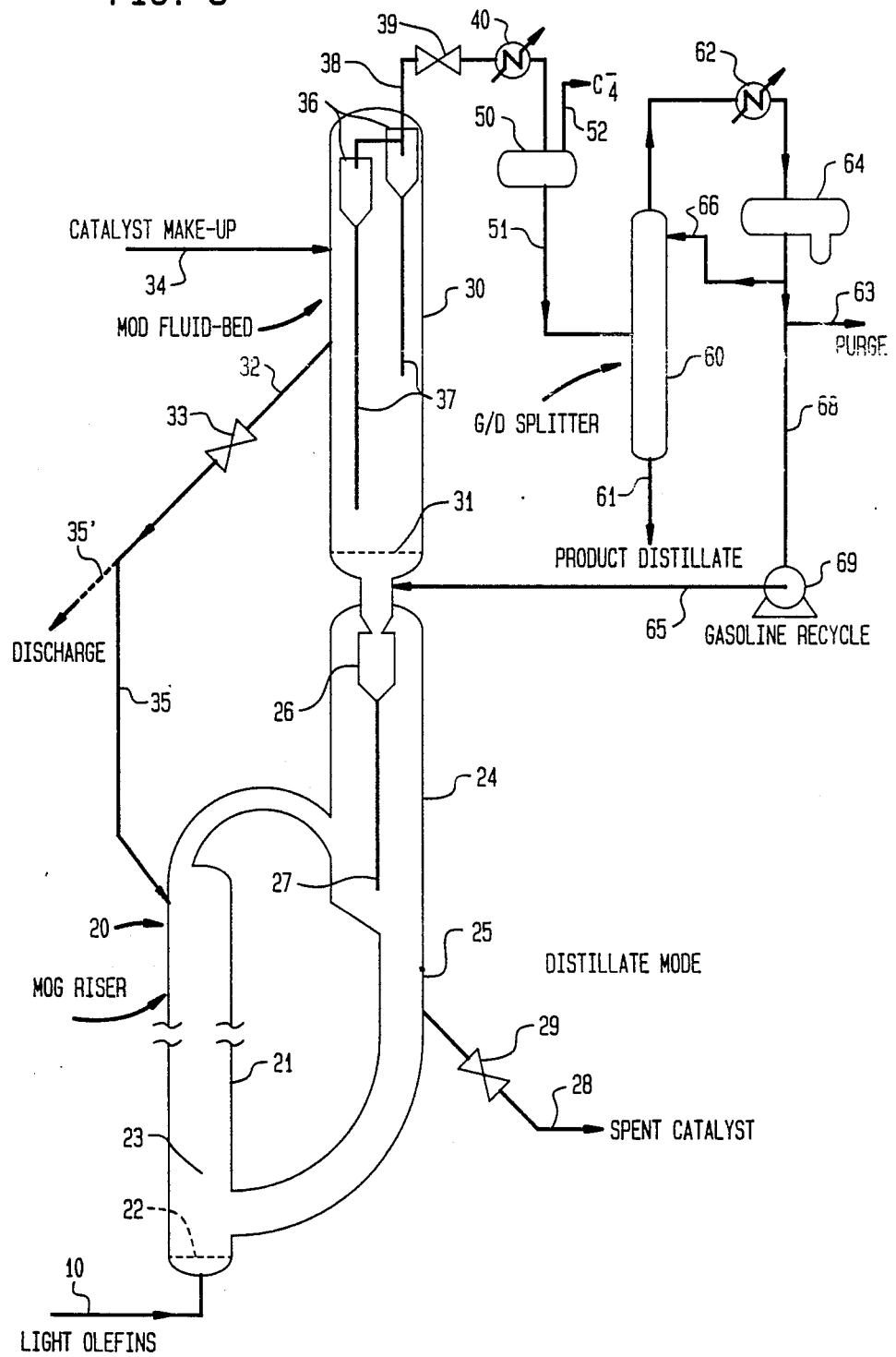

Referring now to FIG. 3, there is illustrated a riser recirc reactor designed to operate by recirculating the catalyst within the reactor, after the catalyst is separated from oligomerized effluent. Though the distribution of particle size is not too important in the operation of the riser, it will be appreciated that the size of catalyst particles is determined by that of the particles in the fluid-bed, where size distribution is important for the fluid-bed's operation in the turbulent regime.

A light-gas feed, rich in $C_3$–$C_4$ olefins passes, through conduit 10, into the MOG reaction vessel indicated generally by reference numeral 20, with the main flow being directed through a bottom inlet of the up-flow portion 21 (so termed because the catalyst flows upwards), of the riser. The feed is distributed through grid plate 22 into the transport zone 23 where catalyst particles are entrained in the feed.

Typically, liquid feed under very high pressure is depressurized into up-flow portion 21 to provide super-dense fluid with the necessary WHSV to transport the particles into separation chamber 24 which is the upper portion of the riser 20. Separation chamber 24 is at or above $P_{max}$ and $T_{max}$. Heat released from the reaction is preferably controlled by adjusting feed temperature. At least one cyclone 26, is provided with a dipleg 27 to return catalyst from the effluent into the down-flow portion 25 so that it can be returned near the bottom of up-flow portion 21. Preferably several sequentially connected cyclones are used. Filters, such as sintered metal plate filters, can be used alone or in conjunction with cyclones. Spent catalyst is withdrawn through line 28 at a desired rate controlled by flow control valve 29. Typically this spent catalyst is used in a FCC cracker (not shown).

An essentially catalyst-free effluent, in an amount sufficient to provide the desired WHSV in MODL reactor 30, is led from the separation chamber 24 into the bottom of the reactor 30 and distributed through a bottom grid 31. Fresh catalyst make-up, as required, is introduced into the MODL reactor 30 through line 34. The reactor 30 is preferably fitted with several cyclones 36 with dip-legs 37 returning catalyst from the effluent to the fluid-bed. Additional separators may be positioned in the upper portion of the reactor 30. An essentially catalyst-free super-dense fluid leaves the vessel 30 through conduit 38 and is depressured in pressure reducing valve 39 so as to form both gas and liquid phases, and further cooled in heat exchanger 40.

Catalyst outlet means 32 is provided for withdrawing catalyst from the fluid-bed in vessel 30. If a separate source of catalyst make-up is available for the MOG riser, the catalyst withdrawn from the MODL is discharged via control valve 33, and through the discharge conduit 35' shown in phantom outline, preferably to a FCC unit (not shown). More typically, withdrawn catalyst is passed through conduit 35, to be used in the riser 20. Since the amount of spent catalyst passed from the MODL to the MOG is relatively small, the temperature of the spent catalyst does not upset the temperature constraints of the riser significantly.

The phases are separated in separator means 50, the gas phase being mainly butenes, e.g. isobutene, and lighter gases ($C_4-$), which is led through conduit 52 to a light ends gas plant (not shown). The recovered liquid hydrocarbon stream comprises mainly $C_5+$ olefins with less than 5% aromatics, some paraffins and naphthenes which flow through conduit 51 to a gasoline/distillate (G/D) splitter 60. Overhead from the G/D splitter is a gasoline stream which is cooled in heat exchanger 62 and flowed into overhead drum 64. A first portion of the gasoline stream is refluxed through reflux line 66 to the upper portion of the G/D splitter. A second portion, in excess of that to be recycled to the MODL, is purged through gasoline purge line 63. A third portion, the gasoline to be recycled, is pumped at sufficiently high pressure by pump 69 and depressured into the bottom of vessel 30 through line 65. Bottoms from the G/D splitter is withdrawn through line 61, and provides the desired distillate product.

Figure 4:
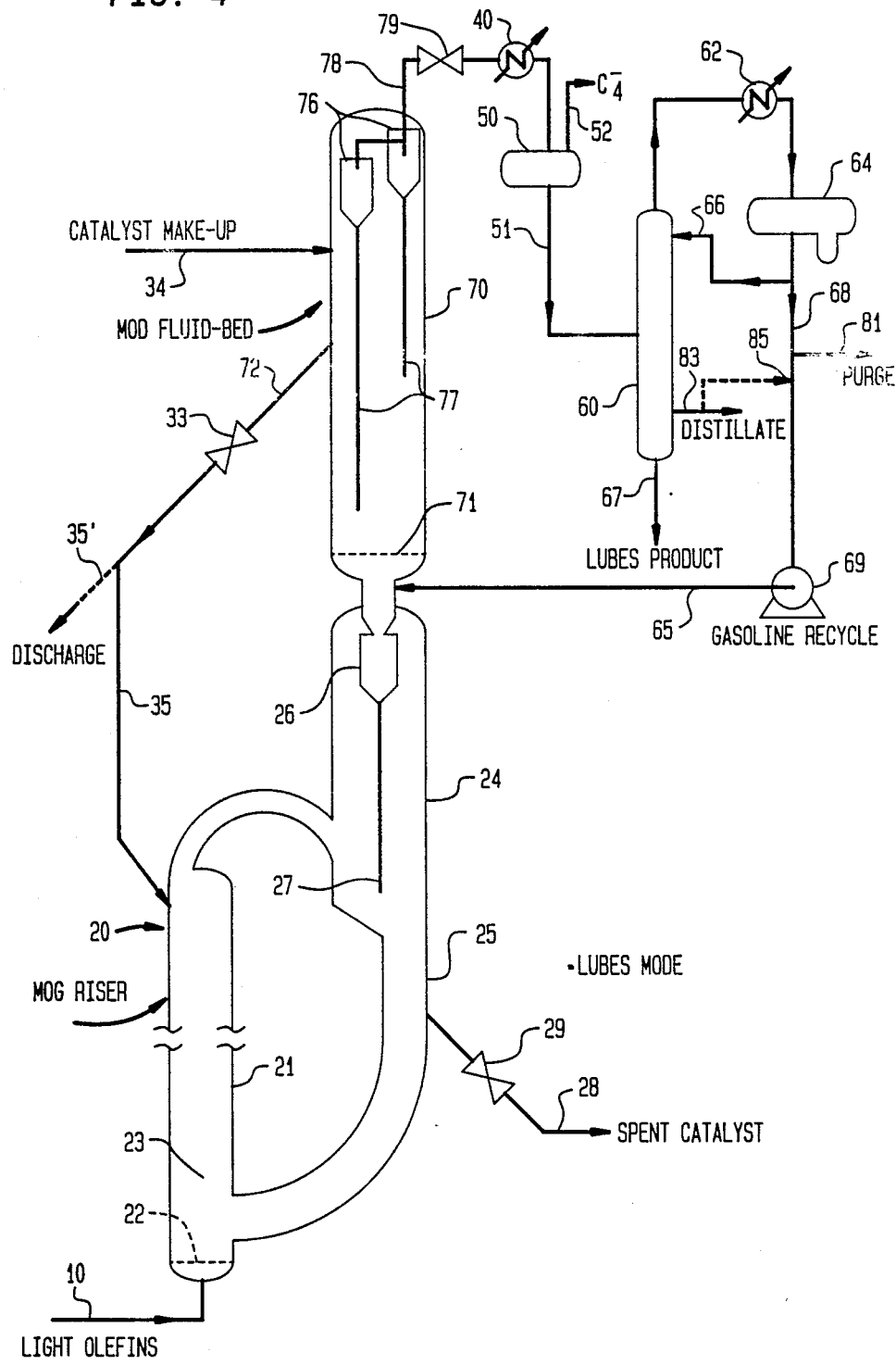
FIG. 4 is a flow diagram for the process in the lubes mode, schematically illustrating the operational relationship of a MOG riser recirc reactor, an MOL fluid-bed reactor, and a fractionator placed downstream of the MOL reactor, to recycle gasoline, optionally with a fraction of distillate, to the MOL reactor. Spent catalyst from the fluid bed MOL and MOG reactors is disposed of as illustrated in FIG. 3 above.

Referring now to FIG. 4, there is schematically illustrated the operation of a MOL reactor 70 in tandem combination with the MOG riser in a manner analogous to that described in FIG. 4. The MOL reactor is fitted with a distributor plate 71, a spent catalyst withdrawal line 72 with a control valve 73 discharging spent catalyst to riser 20 through discharge conduit 72 and optionally to an off-site location through discharge conduit 72'. Fresh catalyst is introduced through make-up line 34, and cyclones 76 having dip-legs 77. The MOL reactor typically operates at higher pressure and lower temperature than the MOD, and in an analogous manner, super-dense effluent leaves through conduit 78 is depressured through valve 79, cooled in the heat exchanger 40, separated and flowed to the G/D splitter 60. However, the splitter is operated to remove an intermediate distillate stream through line 83. A fraction of the distillate in 63 may be recycled to the MOL through conduit 85, shown in phantom outline, the remaining fraction being taken as product distillate. As before, a first portion of the gasoline stream from the top of the G/D column is refluxed through reflux line 66 to the upper portion of the G/D splitter; and, a second portion, in excess of that to be recycled to the MODL, is purged through gasoline purge line 81. The gasoline in line 68 is recycled to the MOL reactor 70 by pressurizing the liquid and depressuring it. The bottoms is desired lubes product withdrawn through line 67.

The MOG and MODL reactors are operable with shape selective medium pore catalysts exemplified by ZSM-5, ZSM-11, ZSM-12, ZSM-23, ZSM-35, ZSM-38, ZSM-48 and other similar materials. ZSM-5 is described in U.S. Pat. No. 3,702,886 [Argauer et al]; ZSM-11 in U.S. Pat. No. 3,709,979 (Chu); ZSM-11 in U.S. Pat. No. 3,832,449 (Rosinski et al); ZSM-22, ZSM-23, ZSM-35, and ZSM-38 in U.S. Pat. Nos. 4,046,859, 4,076,842, and 4,016,245 (Plank et al); and, ZSM-48 in U.S. Pat. No. 4,397,827 (Chu). The disclosures of each of the foregoing are incorporated by reference thereto as if fully set forth herein.

In general the aluminosilicate zeolites are most effectively employed in our MODL reactor. However, zeolites in which some other framework element which is isoelectronic to aluminum and which is present in partial or total substitution of aluminum can be advantageous. Illustrative of elements which can be substituted for part or all of the framework aluminum are boron, gallium, titanium, and, in general, any trivalent metal which is heavier than aluminum. Specific examples of such catalysts include ZSM-5 and zeolite Beta containing boron, gallium and/or titanium. In lieu of, or in addition to, being incorporated into the zeolite framework, these and other catalytically active elements can also be deposited upon the zeolite by any suitable procedure, e.g., by impregnation.

The aluminosilicates are preferred catalysts. These can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

$$M_{2/n}O:Al_2O_3:wSiO_2:YH_2O$$

wherein M represents at least one cation which balances the electrovalence of the tetrahedra, n represents the valence of the cation, w the moles of $SiO_2O$ and Y the moles of $H_2$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluminosilicates are included zeolites, Y, L, S, X, levynite, erionite, faujasite, analcite, paulingite, noselite, phillipsite, datolite, gmelinite leucite, scapolite, mordenite as well as certain caustic treated clays such as montmorillonite and kaolin families. The preferred aluminosilicates are those having pore diameters of greater than about 6 Å (Angstroms).

Aluminosilicates may be treated with a fluid medium or media in a known manner to include a wide variety of aluminosilicates both natural and synthetic which have a crystalline, or, combination of crystalline and amorphous structure. These "promoters" may be provided in the catalyst by impregnation or ion exchange.

Though the process of the invention is operable with any of the aluminosilicates the preferred catalyst is a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 type structures may be utilized by employing highly siliceous materials or crystalline metallosilicate having one or more tetrahedral species having varying degrees of acidity. The ZSM-5 crystalline structure is readily recognized by its X-ray diffraction pattern, which is described in the aforementioned '866 (Argauer, et al.).

While suitable zeolites having a coordinated metal oxide to silica molar ratio of 20:1 to 200:1 or higher may be used, it is advantageous to employ a standard ZSM-5 having a silica:alumina molar ratio of about 25:1 to about 70:1, suitably modified. The oligomerization catalysts preferred for use herein include the medium pore (i.e., about 5–7 Å) shape-selective crystalline aluminosilicate zeolites having a silica-to-alumina ratio of at least 12, a constraint index of about 1 to 12, preferred alpha during operation in the range from about 5 to about 15, and acid cracking activity of about 10–250. A typical zeolite catalyst component having Bronsted acid sitres may consist essentially of aluminosilicate ZSM-5 zeolite with 5 to 95 wt % silica and/or alumina binder.

These siliceous zeolites may be employed in their acid forms, ion exchanged, or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5, suitably modified, having a silica:alumina molar ratio in the range from 12:1 to 100:1, a constraint index in the range from 5 to 12, and with the aforesaid alpha value to convert substantially all the olefins in the feedstock.

ZSM-5 type pentasil zeolites are particularly useful in the process because of their long life and stability under the extreme crystal size from about 0.01 to over 2 microns or more, with 0.02–1 micron being preferred, and an apparent crystal density in the range from about 0.6 to 1.9 $gm/cm^3$. In order to obtain the desired particle size for fluidization in the turbulent regime, the zeolite catalyst crystals are bound with a suitable inorganic oxide, such as silica, alumina, etc. to provide a zeolite concentration of about 5 to 95 wt %.

The average particle density of the catalyst as used may be tailored for optimum fluid-bed operation by compositing it with a matrix component of appropriate density. Such matrix components which provide particles of progressively increasing overall packed density are silica, alumina, beryllia, magnesia, barium oxide, zirconia, and titania, yielding values of from about 2.2 $gm/cm^3$ for silica, up to about 5.9 $gm/cm^3$ for zirconia. In our MODL reactor, the overall packed density of medium pore zeolite particles so composited, including the matrix component, can advantageously vary from about 0.6 to about 4 $gm/cm^3$, more preferably from about 2 to about 3 $gm/cm^3$.

It is advantageous to employ a particle size range consisting essentially of 1 to 200 microns. Average particle size is usually about 20 to 150 microns, preferably 50 to 100 microns. The optimum particle size distribution is obtained with a mixture of larger and smaller particles within the above-specified range, the fluid bed MODL having more fines, up to about 20% by weight, than the MOG riser.

The general operational requirements of a turbulent fluid bed of oligomerization catalyst have been described in our aforementioned pending applications, and are incorporated by reference thereto as if full set forth herein. The requirements for the riser have not. A MODL reactor will typically have a height to diameter ratio of at least 5. A riser reactor will typically have a height to diameter ratio greater than that of a conventional fluid-bed reactor.

It will be appreciated that the design, construction and operating conditions of commercial oligomerization reaction vessels will be dictated by the economics of producing either distillate or lubes, and the optimum operating conditions will be dictated by the conversions sought.

The MOG and MODL reactors are each designed as high-pressure vessels required to contain transport and fluid-bed zones respectively, operating to produce optimum yields of the desired oligomers. The height of the transport zone in the riser is dictated by the higher WHSV required than for the bed of catalyst in the MODL.

Typically, in carrying out the process in the very high pressure MODL reactor, the light gas feed is brought into contact with a medium pore zeolite catalyst having a silica to alumina ratio preferably in the range from 50 to 90, maintained as a super-dense phase in a fluid-bed above $P_{max}$ and at or above $T_{max}$, while the oligomerized effluent from the MOG riser is flowed through the MODL reactor at a superficial vapor velocity in the range from about 0.031 m/sec (0.1 ft/sec) to about 0.616 m/sec (2 ft/sec), preferably from 0.031 m/sec (0.1 ft/sec) to 0.308 m/sec (1 ft/sec). Most preferred superficial velocity is in the range from about 0.1 m/sec (0.3 ft/sec) to about 0.3 m/sec with a HZSM-5 catalyst having a constraint index in the range from 5–12, and, a coke content in the range from about 0.1% to about 1% by wt of catalyst, operating with a WHSV (based on olefin equivalent and total reactor catalyst inventory) in the aforespecified range.

Because operation of the turbulent fluid bed in the super-dense phase produces a remarkably low coking rate, typically less than 0.05 wt % of the olefins in the feed, the MODL reactor may be operated with removal from the system of less than 5% per 24 hr of the inventory of the MODL fluid-bed reactor and the MOG riser reactor.

The effluent from the MOD reactor is tailored by a choice of conditions which produce predominantly $C_{10}^+$–$C_{20}$ oligomers, the ratio of distillate to gasoline range hydrocarbons being in the range from 5:1 to 20:1.

The effluent from the MOL reactor is tailored by a choice of conditions which are deliberately tailored to produce oligomers though, under particular process conditions, as much as about an equal amount by weight of about oligomers (non-lubes) which mainly constitute distillate, may be produced during operation. Typically, the ratio of lubes to non-lubes is 2:1, and may be as much as 20:1.

In the best mode for the production of distillate range hydrocarbons from a light olefinic feedstock having a major proportion by wt of $C_3$–$C_6$ alkenes, the oligomerized product will contain less than about 60% by wt of ($C_{10}^-$) hydrocarbons, and about 40% by wt, or more, of ($C_{10}^+$) hydrocarbons. In most instances, a major portion of the ($C_{10}^-$) hydrocarbons are separated from the product stream and recycled to the super-dense reaction zone.

EXAMPLE

In this illustrative example, a simulated process is carried out in a MOG riser reactor in which a light gas having a predominant amount by weight of monomeric lower $C_3$–$C_6$ olefins is brought into contact with a medium pore HZSM-5 zeolite catalyst having a silica to alumina ratio of about 70. The HZSM-5 catalyst has a constraint index of about 10; in the MOG riser, the equilibrated coke content of the catalyst is about 3% by wt coke; in the MOD fluid bed the equilibrated coke content of the catalyst is about 0.5% by wt coke.

The transport zone in the MOG riser is maintained in the super-dense phase at a pressure of 6300 kPa (915 psia) and, with the inlet temperature of the feed chosen to maintain an operating temperature in the range from about 315.5°-60° C. (600°-680° F.). The light gas is flowed through the MOG reactor at a WHSV of 20 hr$^{-1}$. The major portion of the effluent from the riser is $C_5^+$ but no detailed analysis of the components is made. The results in the Table below are for a single pass.

The fluid-bed in the MOD reactor is maintained in the super-dense phase at a pressure about 69-140 kPa (10-20 psia) lower than the outlet pressure of the MOG riser. The MOG effluent is flowed through the MOD reactor at a WHSV of 0.5 hr$^{-1}$, and a MOD bed temperature in the range from 293°-99° C. (560°-570° F.) is maintained. Though it is preferred to control the temperature in the fluid bed by quenching the effluent from the riser with the gasoline recycle from the G/D splitter, the results below are for a single pass, that is, without any recycle of $C_5$-$C_9$ gasoline range hydrocarbons to the MOD.

The amount of the slipstream from the fluid bed to the riser is varied in the range from about 1% to about 5% by wt per hr, based on the catalyst inventory of the fluid bed, but may be as high as 15% by wt/hr. The slipstream may be taken continuously or intermittently so as to maintain the desired conversion. Fresh make-up catalyst is added to the fluid bed to replenish the fraction of spent catalyst withdrawn; a portion of the make-up may be added to the riser, to enhance the activity of the catalyst.

The analysis for a typical light gas feed and the product distillate recovered from the MOD fluid-bed are presented side-by-side in the Table below.

TABLE

| Light Gas (FCC LPG) | lb/hr, based on fresh feed | |
|---|---|---|
| | FRESH FEED | MOD EFFLUENT |
| $C_2^=$ | 5 | 1 |
| $C_3^=$ | 23.5 | 0 |
| $C_3$ | 7.6 | 8.0 |
| $C_4^=$ | 41.7 | 0.5 |
| $C_4$ | 22.2 | 24.0 |
| $C_5$-$C_{10}$ | 0 | 38.0 |
| $C_{11}^+$ | 0 | 31.5 |
| Total | 100 | 100 |

As is evident from the foregoing example, the total olefins in the feedstream is 70.2 lb/hr; the combined $C_3$-$C_4$ olefins in the MOG effluent is 65.2 lb/hr; the combined $C_3$-$C_4$ olefins in the MOD effluent is 0.5 lb/hr; so that the per pass conversion in the MOG riser and the MOD fluid-bed is better than 95%. Typically, the per pass conversion is over 90%, though in some cases where the olefins are mostly ethene, or the olefin content is relatively low, the per pass conversion may be less.

Having thus provided a general discussion, and a specific illustration of the best mode of operation of tandem super-dense phase MOG riser and MODL turbulent fluid-bed reactors in operation, and described the oligomerization of a predominantly monomeric olefinic light gas feedstream in such a combination of super-dense beds, it is to be understood that no undue restrictions are to be imposed by reason thereof except as provided by the following claims.

We claim:

1. A catalytic process for upgrading a $C_2^+$ olefin feedstream to a heavier product stream rich in $C_{10}^+$ aliphatic hyrocarbons in first and second oligomerization zones, said process comprising, (a) contacting said olefin feedstream in said first zone with a finely divided medium pore size zeolite metallosilicate catalyst ('riser catalyst') having a silica:alumina ratio greater than 12, and a constraint index in the range from about 1 to about 12, at a weight hourly space velocity (WHSV) sufficient to maintain a transport zone, and, then with essentially the same catalyst maintained as a fluid bed, said first zone containing riser catalyst having a higher coke content than that of catalyst in said second zone maintained in a turbulent regime, (b) producing a first distillate-rich gasoline effluent at a pressure above $P_{max}$ and temperature $T_{max}$, under which conditions said first effluent is a super-dense fluid and there is no liquid phase present at least in the upper portion of said transport zone, (c) separating riser catalyst from said first effluent, and separated riser catalyst, without stripping it, within said first oligomerization zone, (d) maintaining said fluid bed with a lower average coke content than that of catalyst in said transport zone, so as to produce a second super-dense effluent having a higher $C_{10}^+$ aliphatic content than that of said first effluent, (e) recovering said $C_{10}^+$ aliphatic hyrocarbons as a mixture which leaves about $P_{max}$ and $T_{max}$ for the mixture, (f) withdrawing a minor fraction of spent fluid bed catalyst from said fluid-bed, (g) replenishing said minor fraction of spent fluid bed catalyst with fresh catalyst, and, (h) withdrawing a minor fraction of spent riser catalyst from said first oligomerization zone; whereby regeneration of spent catalyst is avoided.

2. The process of claim 1 wherein
said olefin feedstream consists essentially of $C_2$-$C_6$ monoolefins, and, said first and second effluents are each above 5600 kPa (800 psia) and 204° C. (400° F.), said second effluent being at lower pressure than said first effluent.

3. The process of claim 2 wherein
said olefin feedstream is maintained at a WHSV in the range above 10 hr$^{-1}$, and said riser zone operates at a density less than 320 kg/m$^3$ (20 lb/ft$^3$);
said first effluent is maintained at a WHSV in the range from about 0.5 hr$^{-1}$ to about 10 hr$^{-1}$ in said fluid bed, and said fluid bed operates at a bed density, measured at the bottom, greater than 160 kg/m$^3$ (10 lb/ft$^3$);
the fines content of riser catalyst in the transport zone is less than about 15% by wt, based on the weight of the catalyst in the bed, and, the fines content of fluid-bed catalyst is in the range from about 10% to about 20% by wt, said fines having a particle size less than 32 microns.

4. The process of claim 2 wherein the average coke content of catalyst in the fluid bed is less than 15% by wt, based on the weight of catalyst; and the average coke content of riser catalyst is greater than 1% and higher than the average coke content of the fluid bed catalyst.

5. The process of claim 3 wherein said catalyst has a constraint index in the range from 5 to about 12, is added to the fluid bed as fresh catalyst having activity alpha in the range from 50 to about 600, and said silica:alumina ratio is in the range from about 12:1 to 70:1.

6. The process of claim 4 wherein said $C_2$-$C_6$ monoolefins comprise a major proportion by weight of propene and butenes.

7. The process of claim 4 wherein said fluid bed is maintained in a reaction zone operated in a distillate mode at a pressure in the range from about 5600 kPa to about 6750 kPa (815–980 psia), and a temperature in the range from 260° C. to about 343° C. (500° F.–650° F.); and, said $C_{10}+$ aliphatic hydrocarbons consist essentially of distillate, boiling in the range from about 138° C. to about 349° C. (280° F.–660° F.).

8. The process of claim 4 wherein said fluid bed is maintained in a reactor operated in a lubes mode at a pressure in the range from about 6300 kPa to about 6890 kPa (915–1000 psia), and a temperature in the range from 205° C. to about 316° C. (400° F.–600° F.); and, said $C_{10}+$ aliphatic hydrocarbons consist essentially of lubes having a viscosity in the range from 4 cp to about 40 cp, measured at 100° C.

9. The process of claim 4 wherein said monoolefin feedstream is essentially free of hydrogen.

10. A catalytic process for upgrading a $C_2+$ olefin-containing feedstream to a heavier product stream rich in $C_{10}+$ aliphatic hydrocarbons, said process comprising, (a) operating separate transport and turbulent regime oligomerization zones directly combined in tandem as riser and fluid bed zones containing riser catalyst and fluid bed catalyst respectively, the pressure in the riser being higher than that in the fluid bed, with the hydrocarbons at least in the upper portion of the riser, and those in the fluid bed being in the super-dense phase, (b) contacting said feedstream, at a sufficiently high WHSV to maintain the riser zone, with a solid, finely divided medium pore size zeolite metallosilicate riser catalyst having a higher average coke content and an equilibrated activity less than that of essentially the same catalyst in the fluid bed, (c) producing a distillate-rich gasoline effluent which leaves said riser zone in the super-dense phase, (d) contacting said distillate-rich gasoline effluent in said fluid bed with catalyst which has a lower coke content than catalyst in said riser zone, said fluid bed operating at a sub-transport WHSV, and above a pressure $P_{max}$ and temperature $T_{max}$ for hydrocarbons within said fluid-bed, so that there is no liquid phase present in said second reaction zone, (e) producing a $C_{10}+$-rich aliphatic hyrocarbon heavies effluent which leaves in the super-dense phase from said fluid bed, (f) recovering $C_{10}+$ aliphatic hyrocarbons from said heavies effluent, (g) transferring a minor fraction of spent fluid bed catalyst from said fluid bed to said riser, without stripping said catalyst, (h) removing and not returning to either zone, a minor fraction of spent catalyst from said riser, and, (i) replenishing said fluid bed with fresh catalyst in a replacement amount corresponding to spent riser catalyst removed, so as to maintain catalyst in said fluid-bed at desired activity; whereby regeneration of spent catalyts is avoided.

11. The process of claim 10 wherein
said olefin feedstream consists essentially of $C_2$-$C_6$ monoolefins, and, said first and second effluents are each above 5600 kPa (800 psia) and 204° C. (400° F.), said second effluent being at lower pressure than said first effluent.

12. The process of claim 11 wherein
said olefin feedstream is maintained at a WHSV in the range above 10 hr$^{-1}$, and said riser zone operates at a density less than 320 kg/m$^3$ (20 lb/ft$^3$);
said first effluent is maintained at a WHSV in the range from about 1 hr$^{-1}$ to about 10 hr$^{-1}$ in said fluid bed, and said fluid bed operates at a bed density, measured at the bottom, greater than 160 kg/m$^3$ (10 lb/ft$^3$);
the fines content of riser catalyst in the transport zone is less than about 15% by wt, based on the weight of the catalyst in the riser, and, the fines content of fluid-bed catalyst is in the range from about 10% to about 20% by wt, said fines having a particle size less than 32 microns.

13. The process of claim 12 wherein the average coke content of catalyst in the fluid bed is less than 15% by wt, based on the weight of catalyst; and the average coke content of riser catalyst is greater than 1% and higher than the average coke content of the fluid bed catalyst.

14. The process of claim 13 wherein said catalyst has a constraint index in the range from 5 to about 12, is added to the fluid bed as fresh catalyst having activity alpha in the range from 50 to about 600, and said silica:alumina ratio is in the range from about 12:1 to 70:1.

15. The process of claim 13 wherein said $C_2$-$C_6$ monoolefins comprise a major proportion by weight of propene and butenes.

16. The process of claim 13 said fluid bed is maintained in a reaction zone operated in a distillate mode at a pressure in the range from about 5600 kPa to about 6750 kPa (815–980 psia), and a temperature in the range from 260° C. to about 343° C. (500° F.–650° F.); and, said $C_{10}+$ aliphatic hydrocarbons consist essentially 349° C. (280° F.–660° F.).

17. The process of claim 13 wherein said fluid bed is maintained in a reactor operated in a lubes mode at a pressure in the range from about 6300 kPa to about 6890 kPa (915–1000 psia), and a 600° F.); and, said $C_{10}+$ aliphatic hydrocarbons consist essentially of lubes having a viscosity in the range from 10 cp to about 100 cp, measured at 100° C.

18. The process of claim 12 wherein said monoolefin feedstream is essentially free of hydrogen.

19. A process for oligomerizing a "light gas" feedstream containing $C_2$-$C_6$ lower olefins and diluent $C_2$-$C_6$ paraffins, to $C_{10}+$ "heavies", comprising, (a) operating at least the upper portion of a riser zone of finely divided medium pore zeolite metallosilicate catalyst having a silica:alumina ratio greater than 12, and a constraint index in the range from about 1 to 12, at or above a temperature $T_{max}$ and a pressure $P_{max}$ at which no liquid may form; whereby a distillate-rich gasoline first effluent in the super-dense phase is produced;

(b) directly flowing said first effluent, without stripping it, to a super-dense fluid bed of said catalyst having a lower average coke content than catalyst in the riser, so as to produce a heavies effluent containing $C_{10}+$ hydrocarbons;

(c) separating and recovering gasoline from the $C_{10}+$ hydrocarbons in the heavies effluent, said $C_{10}+$ being present in a major amount by weight relative to that of said lower olefins in the heavies effluent;

(d) returning at least some of the gasoline to the fluid bed to control the temperature of the first effluent;

(e) withdrawing a minor fraction of spent fluid bed catalyst from said fluid bed;

(f) replenishing said minor fraction of spent fluid bed catalyst with fresh catalyst; and, (g) withdrawing a minor fraction of spent riser catalyst from said first oligomerization zone; whereby regeneration of spent catalyst is avoided.

20. The process of claim 19 wherein said fluid bed is maintained in a reaction zone operated in a distillate mode at a pressure in the range from about 5600 kPa to about 6750 kPa (815-980 psia), and a temperature in the range from 260° C. to about 343° C. (500° F.- 650° F.); and, said $C_{10}+$ aliphatic hydrocarbons consist essentially of distillate, boiling in the range from about 138° C. to about 349° C. (280° F.-660° F.).

21. The process of claim 19 wherein said fluid bed is maintained in a reactor operated in a lubes mode at a pressure in the range from about 6300 kPa to about 6890 kPa (915-1000 psia), and a temperature in the range from 205° C. to about 316° C. (400° F.-600° F.); and, said $C_{10}+$ aliphatic hydrocarbons consist essentially of lubes having a viscosity in the range from 4 cp to about 40 cp, measured at 100° C.

22. The process of claim 19 wherein said catalyst is a siliceous metallosilicate acid zeolite having a ZSM-5 structure; said constraint index is in the range from 5 to about 12; said silica:alumina ratio is in the range from about 12:1 to 70:1; activity alpha for catalyst in the fluid bed is in the range from 10 to about 600; and an alpha for catalyst in the transport zone is in the range from 1 to about 10.

23. The process of claim 19 wherein said catalyst withdrawn from the fluid bed is flowed to the riser; from about 1% to about 15% by wt per hour of the inventory of fluid bed catalyst is withdrawn from the fluid bed; and said catalyst withdrawn from the riser is neither regenerated nor returned to either the riser or the fluid bed.

24. The process of claim 20 wherein the olefin content of said first effluent is $C_5=+$, and the pentane to pentene ratio in the first effluent is less than 0.4.

* * * * *

UNITED STATES PATENT AND TRADEMARK OFFICE
CERTIFICATE OF CORRECTION

PATENT NO. : 4,926,003

DATED : May 15, 1990

INVENTOR(S) : Harandi and Owen

It is certified that error appears in the above-identified patent and that said Letters Patent is hereby corrected as shown below:

Column 24, Line 33, add "wherein" after "Claim 13"

Column 24, Line 39, add "of distillate, boiling in the range from about 138°C to about" after "essentially"

Column 24, Line 43, delete "600°F" and add "temperature in the range from 205°C to about 316°C (400°F - 600°F);"

Signed and Sealed this

Eighth Day of October, 1991

Attest:

HARRY F. MANBECK, JR.

Attesting Officer

Commissioner of Patents and Trademarks